(12) United States Patent
Ineson

(10) Patent No.: US 6,616,658 B2
(45) Date of Patent: Sep. 9, 2003

(54) ELECTROSURGICAL PENCIL

(76) Inventor: Leonard Ineson, 3574 Pine Pitch Crescent, Mississauga, Ontario (CA), L5L 1P8

( * ) Notice: Subject to any disclaimer, the term of this patent is extended or adjusted under 35 U.S.C. 154(b) by 0 days.

(21) Appl. No.: 09/986,449

(22) Filed: Nov. 8, 2001

(65) Prior Publication Data

US 2003/0088247 A1 May 8, 2003

(51) Int. Cl.⁷ .............................................. A61B 18/18
(52) U.S. Cl. .............................. 606/42; 606/45; 606/49
(58) Field of Search ............................. 606/32, 34, 39, 606/40, 41, 42, 45, 49–52

(56) References Cited

U.S. PATENT DOCUMENTS

| 5,085,657 | A | * | 2/1992 | Ben-Simhon | 606/42 |
|---|---|---|---|---|---|
| 5,431,650 | A | | 7/1995 | Cosmescu | |
| 5,693,044 | A | * | 12/1997 | Cosmescu | 606/42 |
| 5,800,431 | A | | 9/1998 | Brown | |
| 5,836,944 | A | | 11/1998 | Cosmescu | |
| 5,951,548 | A | * | 9/1999 | DeSisto et al. | 606/42 |
| 6,099,525 | A | | 8/2000 | Cosmescu | |
| 6,117,134 | A | | 9/2000 | Cunningham et al. | |
| 6,142,995 | A | | 11/2000 | Cosmescu | |
| 6,146,353 | A | * | 11/2000 | Platt, Jr. | 604/22 |
| 6,149,648 | A | | 11/2000 | Cosmescu | |
| 6,258,088 | B1 | | 7/2001 | Tzonev et al. | |

* cited by examiner

Primary Examiner—Roy D. Gibson
Assistant Examiner—Peter J Vrettakos

(57) ABSTRACT

An electrosurgical pencil comprises a main body portion forming a handle. A wire retaining passage is defined by the main body portion and has a wire-receiving opening and an electrode-receiving opening. A metal electrode tip is mounted at the electrode-receiving opening for engaging tissue in a surgical site to thereby coagulate the tissue. A wire enters the wire retaining passage is selectively connectable in electrically conductive relation through an electrical switch to the metal electrode tip. A substantially unobstructed airflow vent is defined substantially solely by the main body portion so as to extend from the electrode end to the exhaust end of the main body portion, and has an inlet disposed adjacent the electrode end of the main body portion and that is connected in fluid communication via the airflow vent to an outlet disposed adjacent the exhaust end of the main body portion.

30 Claims, 3 Drawing Sheets

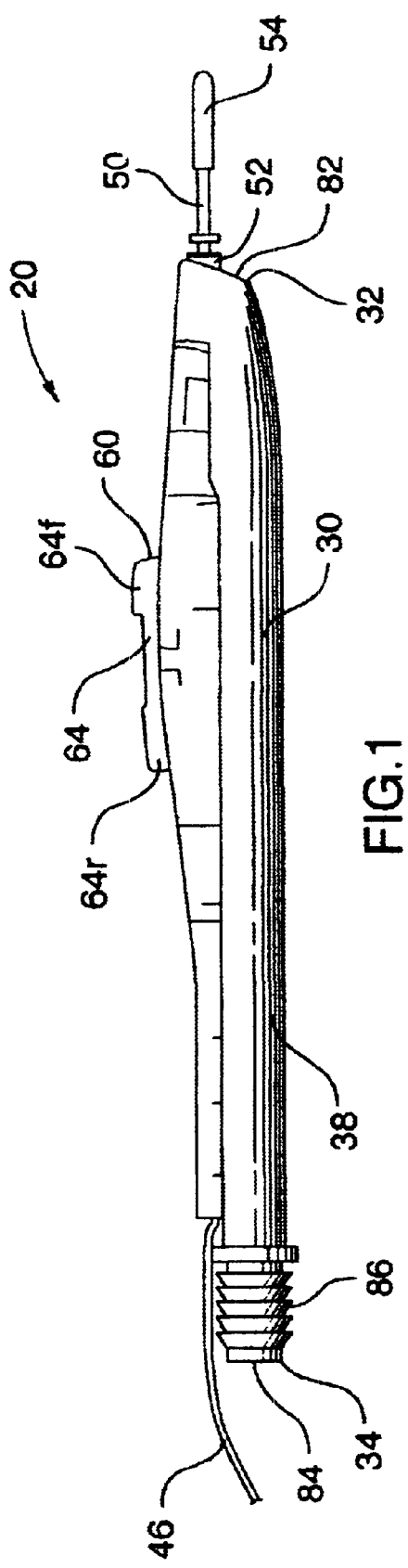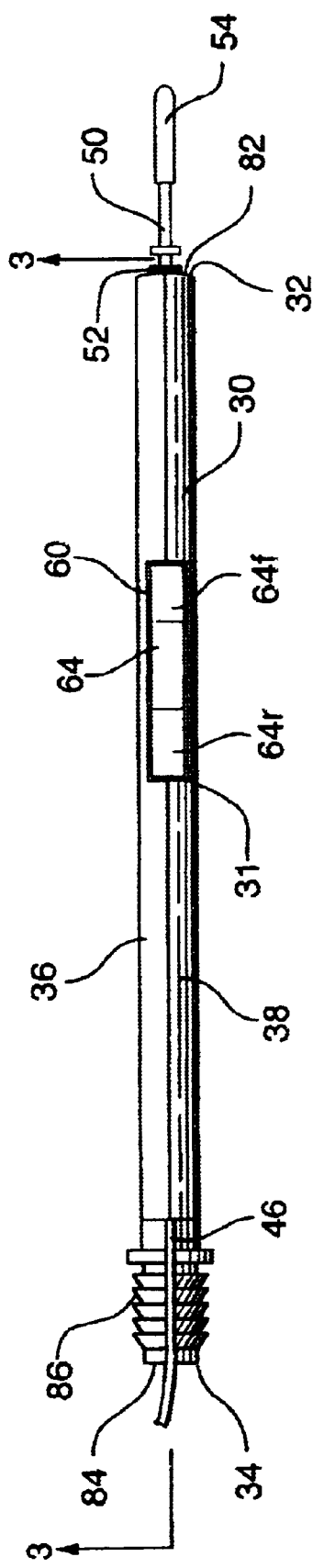

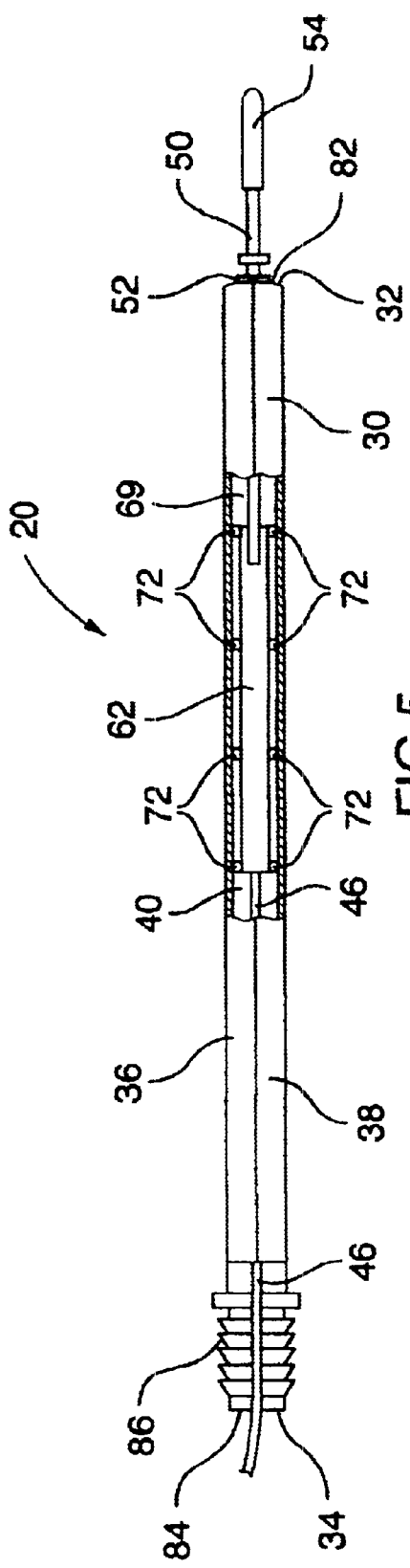
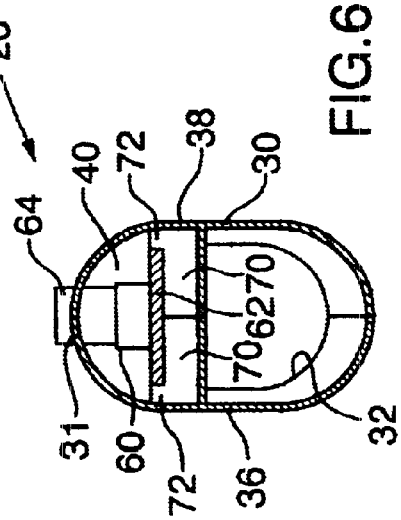
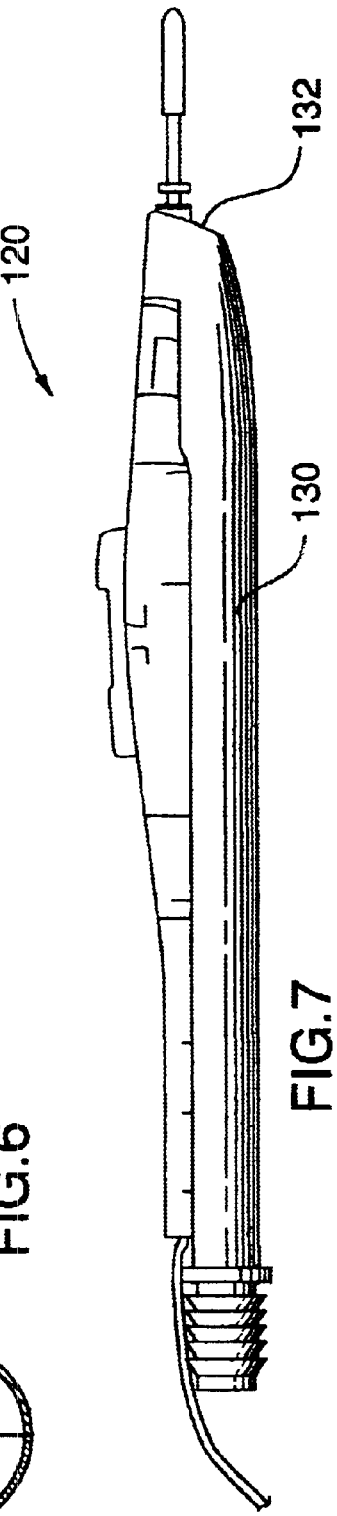
FIG.5
FIG.6
FIG.7

ELECTROSURGICAL PENCIL

FIELD OF THE INVENTION

The present invention relates to electrosurgical instruments and more particularly to electrosurgical pencils for cauterizing tissue and evacuating smoke from a surgical site.

BACKGROUND OF THE INVENTION

The coagulation of blood vessels is a necessary part of medical surgery and is commonly performed by an electrosurgical tool commonly known as an electrosurgical pencil or coagulator pencil. In an electrosurgical pencil, a electrically conductive metal tip, usually flat in shape, extends outwardly from the end of the body of a hollow plastic main body that acts as a hand grip for a surgeon using the electrosurgical tool. In use, the tissue of a patient is electrically connected to one side of an electrosurgical circuit, and the electrically conductive tip is connected to the other side of the electrosurgical circuit. When the metal tip touches or is near the tissue at the surgical site, a high frequency electrical current flows from the electrode to the tissue, thus coagulating and cauterizing the tissue.

Due to the cauterizing effect of the electrically conductive metal tip, small plumes of smoke are produced, which are typically referred to as surgical smoke and must be removed. This surgical smoke is offensive in terms of its pungent odour, and is also potentially dangerous to surgeons and other operating room staff in that it contains possible carcinogenic elements, and also potentially contains transportable viable viral DNA. Exacerbating this problem, is the fact that such plumes of smoke tend to rise plumes toward the persons involved in the operation. Further, the evacuation of smoke away from the surgical site is vital so that the surgeon's view of the operation site remains as unobscured as reasonably possible.

In order to evacuate smoke from a surgical site, some prior art electrosurgical pencils are constructed to have an air flow passage with an inlet that either terminates adjacent the metal tip or is in fluid communication with the metal tip, and an outlet at the opposite end. The outlet is configured to receive and retain thereon a plastic air flow hose that is connected to a source of low air pressure that causes air to be drawn from the electrosurgical pencil. The air flow must be sufficient to draw away plumes of surgical smoke.

One problem with such prior art electrosurgical tools is that they have unnecessarily complicated structures, and are typically constructed from several parts. Further, many of the parts are unduly robust for use in a disposable tool. Accordingly, such prior art electrosurgical tools are expensive, which is highly undesirable, especially considering that the present day health care system in general, and hospitals in particular, are under severe budget constraints.

Also, it has been found in the prior art that electrosurgical tools having integral structures for smoke evacuation usually provide inadequate air flow. For such evacuation, the amount of air flow (commonly measured in cubic feet per minute) is greatly improved through the present invention.

Further, the air flow path that the surgical smoke is evacuated through is defined by several elements, thus, adding to the cost and complexity and contributing to the problem of a narrow air flow passage.

U.S. Pat. No. 6,117,134 issued Sep. 12, 2000 to Cunningham et al, discloses an Instrument for Suction Electrosurgery. This instrument has an elongate body 11 molded from polymer plastic. A main flow passage 14 extends from a connecting nipple 12 at its back end to its front end where it diverts to a narrow forward main passage section 18 and to a branch passage 20 that extends to an elongate vent 22 that is used to control air flow through the passage 14. A hollow metal electrode tip 30 is inserted into the narrow forward main passage section 18 of the main flow passage 14. The hollow metal tube electrode tip 30 is electrified by means of a wire 26 disposed within a second passageway 24, with the leading end of the wire 26 having a spade connector 29 crimped thereon, which spade connector 29 is clamped in place by the hollow metal tube 30, thus electrically connecting the hollow metal tube 30 to an electrical power source. Smoke is evacuated from a surgical site through the hollow metal tube's electrode tip 30, into the forward portion of the main passage section 18, into the main passage 14, through the nipple 12, and into a flexible tube connected thereto. The limited cross-section of this air flow path ensures that the evacuation of surgical smoke is not maximized. Further, this prior art electrosurgical pencil has a main body that is very robust and that must be made from several molded pieces secured together, typically by a suitable adhesive or by ultrasonic welding. Further, the air flow path exists in part, within the electrode itself, thus precluding this particular prior art electrosurgical pencil from reaching maximum air flow.

U.S. Pat. No. 6,149,648 issued Nov. 21, 2000 to Cosmescu discloses an Electrosurgical Unit Argon Beam Coagulator Pencil Apparatus and Method for Operating Same. Wherein the coagulator pencil apparatus 21 comprises a handpiece 22 having a nozzle assembly 11 mounted thereon via tubing 9, with an electrode 12 removably coupled within a socket 8 and surrounded by the nozzle assembly 11. An exhaust connector 13 is coupled to the proximal end of the handpiece 22. At the proximal end of the connector 13 there is namely an exhaust port 15 that is connectable to a source of low air pressure. In use, smoke is drawn through the nozzle assembly 11 into the tubing 9 and then into the exhaust connector 13, through the exhaust port 15 and into tubing (not shown). This particular electrosurgical unit has a large number of components, many of which components define the air flow path, and is somewhat intricate, and is therefore unduly expensive. Further, the cross-sectional area of the air flow path is quite small and is also not straight, thus ensuring that the evacuation of surgical smoke is not maximized.

U.S. Pat. No. 5,800,431 issued Sep. 1, 1998 to Brown, discloses an Electrosurgical Tool with Suction and Cautery. The electrosurgical tool 2 has a handle 4 having an internal passage 10 that leads from a connector 16, to a tube 18 and to a source of low air pressure. The forward end of the internal passage 10 connects to an air passage that is in fluid communication with a port 12 at the front end 8 of the electrosurgical tool 2. A heatable tip 6 extends outwardly from the vicinity of the port 12. The passage 10 is defined by tubing in the rear portion and in the front portion, which pieces of tubing are connected by a block of material whereat the internal passage 10 is of a restricted diameter. The cross-sectional area of the internal passage of this electrosurgical tool is quite limited due to its specific construction, which is highly undesirable. Further, there are several components that define the air flow path, which makes this prior art electrosurgical tool unnecessarily expensive.

U.S. Pat. No. 5,951,548 issued Sep. 14, 1999 to DeSisto et al discloses a self evacuating electrocautery device having a hollow body 12 having an outlet connected to vacuum tubing 20, which is in turn connected to a source of low air pressure. A disposable electrocautery blade 16 is inserted into the forward end of the hollow body 12 and terminates within a first air passageway 54. A plurality of plume intake ports 52 permit passage of smoke into the first passageway 54 past spaced ribs 38. The first passageway 54 is connected through an intermittent self-centering rocker switch 14 to a second airway path 56 which leads to the vacuum tubing 20. The specific multi-component configuration of the first airway path 54 especially at the intake ports 52 and the spaced ribs 38 tend to restrict the flow of air therethrough and also make the hollow body 12 of the electrocautery device 10 expensive and difficult to manufacture.

It is an object of the present invention to provide an electrosurgical pencil that evacuates smoke from a surgical site, wherein the smoke evacuation structure is integrally formed within the electrosurgical pencil, and that is inexpensive to manufacture.

It is another object of the present invention to provide an electrosurgical pencil that evacuates smoke from a surgical site, wherein the smoke evacuation structure is integrally formed within the electrosurgical pencil, and that provides maximized air flow.

It is a further object of the present invention to provide an electrosurgical pencil that evacuates smoke from a surgical site, wherein the smoke evacuation structure is integrally formed within the electrosurgical pencil, and wherein the air flow path for evacuation of surgical smoke is defined by the main body only.

SUMMARY OF THE INVENTION

In accordance with one aspect of the present invention there is disclosed a novel electrosurgical pencil for use in performing surgery on a surgical site. The electrosurgical pencil comprises a main body portion forming a handle grippable by a user, and has an electrode end, and an exhaust end. A wire retaining passage is disposed within the main body portion and has a wire-receiving opening and an electrode-receiving opening. A metal electrode tip is mounted on main body portion at the electrode-receiving opening for engaging tissue in a surgical site to thereby cut or coagulate the tissue. An electrical switch means is mounted on the main body portion so as to be operable externally to the main body portion. A wire enters the wire retaining passage through the wire-receiving opening and is selectively connectable in electrically conductive relation through the electrical switch means to the metal electrode tip. A substantially unobstructed airflow vent is disposed within the main body portion and has an inlet disposed adjacent the electrode end of the main body portion and that is connected in air flow communication via the airflow vent to an outlet disposed adjacent the exhaust end of the main body portion. The substantially unobstructed air flow vent permits maximized air flow for the removal of surgical smoke. The outlet is connectable in fluid communication via flexible tubing to a source of low air pressure, to thereby permit evacuation of surgical smoke into the inlet of the airflow vent, through the airflow vent, and out the outlet of the airflow vent.

In accordance with another aspect of the present invention there is disclosed a novel electrosurgical pencil for use in performing surgery on a surgical site. The electrosurgical pencil comprises a main body portion forming a handle grippable by a user, and has a electrode end, and an exhaust end. A wire retaining passage is defined by the main body portion and has a wire-receiving opening and an electrode-receiving opening. A metal electrode tip is mounted on main body portion at the electrode-receiving opening for engaging tissue in a surgical site to thereby cut or coagulate the tissue. An electrical switch means is mounted on the main body portion so as to be operable externally to the main body portion. A wire enters the wire retaining passage through the wire-receiving opening and is selectively connectable in electrically conductive relation through the electrical switch means to the metal electrode tip. An airflow vent is defined by the main body portion so as to extend from the electrode end to the exhaust end of the main body portion, and has an inlet disposed adjacent the electrode end of the main body portion and connected in air flow communication via the airflow vent to an outlet disposed adjacent the exhaust end of the main body portion. The air flow vent permits maximized air flow for the removal of surgical smoke. The outlet is connectable in fluid communication via flexible tubing to a source of low air pressure, to thereby permit evacuation of surgical smoke into the inlet of the airflow vent, through the airflow vent, and out the outlet of the airflow vent.

In accordance with one aspect of the present invention there is disclosed a novel electrosurgical pencil for use in performing surgery on a surgical site. The electrosurgical pencil comprises a main body portion forming a handle grippable by a user, and has an electrode end, and an exhaust end. A wire retaining passage is disposed within the main body portion and has a wire-receiving opening and an electrode-receiving opening. A metal electrode tip is mounted on main body portion at the electrode-receiving opening for engaging tissue in a surgical site to thereby cut or coagulate the tissue. An electrical switch means is mounted on the main body portion so as to be operable externally to the main body portion. A wire enters the wire retaining passage through the wire-receiving opening and is selectively connectable in electrically conductive relation through the electrical switch means to the metal electrode tip. A airflow vent is substantially solely defined by the main body portion. The airflow vent has an inlet disposed adjacent the electrode end of the main body portion and that is connected in air flow communication via the airflow vent to an outlet disposed adjacent the exhaust end of the main body portion. The substantially unobstructed air flow vent permits maximized air flow for the removal of surgical smoke. The outlet is connectable in fluid communication via flexible tubing to a source of low air pressure, to thereby permit evacuation of surgical smoke into the inlet of the airflow vent, through the airflow vent, and out the outlet of the airflow vent.

Other advantages, features and characteristics of the present invention, as well as methods of operation and functions of the related elements of the structure, and the combination of parts and economies of manufacture, will become more apparent upon consideration of the following detailed description and the appended claims with reference to the accompanying drawings, the latter of which is briefly described herein below.

BRIEF DESCRIPTION OF THE DRAWINGS

The novel features which are believed to be characteristic of the electrosurgical pencil according to the present invention, as to its structure, organization, use and method of operation, together with further objectives and advantages thereof, will be better understood from the following drawings in which a presently preferred embodiment of the invention will now be illustrated by way of example. It is expressly understood, however, that the drawings are for the purpose of illustration and description only, and are not intended as a definition of the limits of the invention. In the accompanying drawings:

FIG. 1 is a side elevational of the preferred embodiment of the electrosurgical pencil according to the present invention;

FIG. 2 is a top plan view of the electrosurgical pencil of FIG. 1;

FIG. 5 is a partially sectioned top plan view taken along section line 5—5 of FIG. 3;

FIG. 6 is an enlarged scale cross-sectional end elevational view taken along section line 6—6 of FIG. 3; and, FIG. 7 is a side elevational view of a first alternative embodiment of the electrosurgical pencil according to the present invention.

DETAILED DESCRIPTION OF A PREFERRED EMBODIMENT

Figure 3:
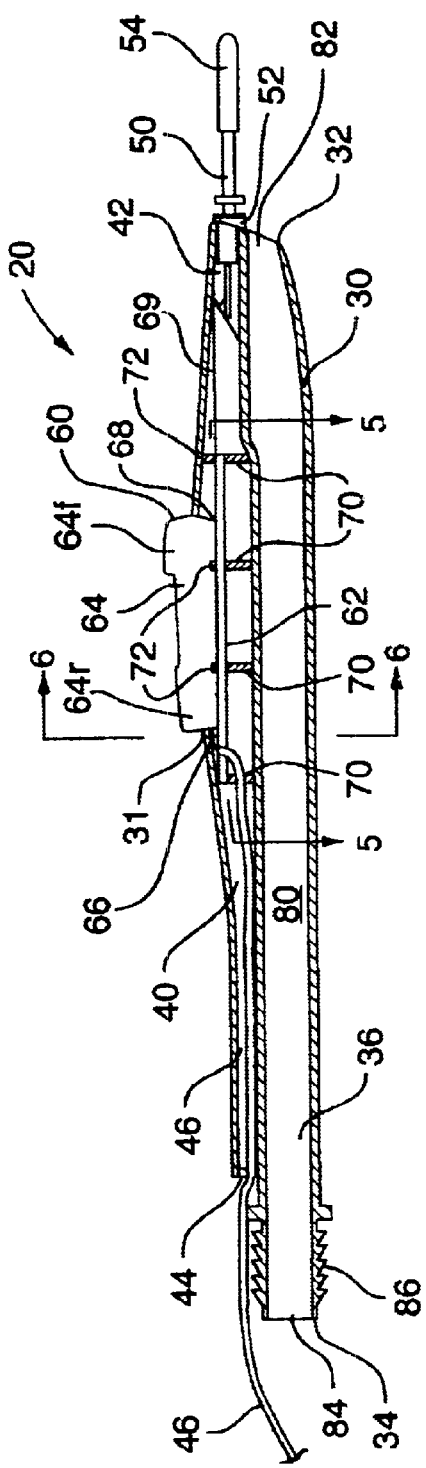
FIG. 3 is a cross-sectional side elevational view taken along section line 3—3 of FIG. 2.

Referring to FIGS. 1 through 7 of the drawings, it will be noted that FIGS. 1 through 6 illustrate a preferred embodiment of the electrosurgical pencil of the present invention, and FIG. 7 illustrates an alternative embodiment of the electrosurgical pencil of the present invention.

Reference will now be made to FIGS. 1 through 6, which show a preferred embodiment of the electrosurgical pencil according to the present invention, as indicated by the general reference numeral 20, for use in performing surgery on a surgical site. The preferred embodiment electrosurgical pencil 20 comprises a main body portion 30 forming a handle grippable by a user. The main body portion 30 is preferably shaped in an manner to conform to a user's hand, for the purpose of comfort and ease of use. The main body portion 30 has an electrode end 32 and an exhaust end 34.

In order to make the electrosurgical pencil 20 economical and light in weight, the main body portion 30 is made from a suitable plastic material, such as polyethylene. In the preferred embodiment illustrated, the main body portion 30 comprises two components, namely a left half 36 and a right half 38, as can be best sen in FIGS. 2, 5 and 6. The left and right halves 36,38 are joined together by means of ultrasonic welding, as is known in the plastics industry.

An elongate wire-retaining passage 40 is disposed within the main body portion 30, and more specifically, is defined by the main body portion 30. The wire-retaining passage 40 has an electrode-receiving opening 42 disposed at the electrode end 32 of the main body portion 30. Similarly, a wire-receiving opening 44 is disposed at the exhaust end 34 of the main body portion 30.

A metal electrode tip 50 has a plastic base 52 and a pliable plastic end covering 54, and is removably mounted on the main body portion 30 at the electrode-receiving opening 42. The metal electrode tip 50 is for engaging tissue in a surgical site, to thereby cut or coagulate the tissue, as is well known in the medical field.

An electrical switch means comprising a single-pole double-throw rocker type electrical switch 60 is mounted on a small circuit board 62. The circuit board 62 is mounted within the wire-retaining passage 40 such that the circuit board 62 is seated on a plurality of flanges 70, as can be best seen in FIGS. 3 through 6, so as to be frictionally retained between opposed raised portions 72 of the flanges 70. The rocker portion 64 of the rocker type electrical switch 60 extends through a co-operating opening 31 in the main body portion 30. In this manner, the rocker type electrical switch 60 is mounted on the main body portion 30 so as to be operable externally to the main body portion 30, by a physician during surgery. In use, the forward portion 64f of the rocker portion 64 is pressed to provide a higher frequency signal to the metal electrode tip 50 for cutting tissue, as indicated by arrow "A" in FIG. 4, and the rearward portion 64r of the rocker portion 64 is pressed to provide a lower frequency signal to the metal electrode tip 50 for cauterizing tissue. Alternatively, two push-button type switches could be used in place of the rocker type electrical switch 60.

An insulated wire 46 enters the wire-retaining passage 40 through the wire-receiving opening 44. The wire 46 is connected in electrically conductive relation to one terminal 66 of the rocker type electrical switch 60. The other terminal 68 of the rocker type electrical switch 60 is connected in electrically conductive relation to the metal electrode tip 50 via an electrical contact 69. In this manner, the wire 46 is selectively connectable in electrically conductive relation through the electrical switch means 60 to the metal electrode tip 50.

An elongate substantially unobstructed airflow vent 80 is disposed within the main body portion 30, so as to extend from the electrode end 32 to the exhaust end 34 of the main body portion 30. In the preferred embodiment, and as can be best seen in FIGS. 3, 4 and 6, the airflow vent 80 is defined by the main body portion 30, and more specifically, the elongate airflow vent 80 is substantially solely defined by the main body portion 30. In other words, the airflow vent 80 is not defined by a mechanical type switch, nor by a extra tubing, or the like, as in the prior art. Further, the airflow vent 80 is sealed off from the wire-retaining passage 40 by horizontal walls 31a and 31b, thus precluding any smoke or other tissues or liquids from reaching the electrical parts of the electrosurgical pencil 20, such as the rocker type electrical switch 60, the circuit board 62, and the wire 46.

The elongate substantially unobstructed airflow vent 80 has an inlet 82 disposed adjacent the electrode end 32 of the main body portion 30. The inlet 82 is connected in air flow communication via the airflow vent 80 to an outlet 84 disposed adjacent the exhaust end 34 of the main body portion 30. The substantially unobstructed airflow vent 80 permits maximized air flow for the removal of surgical smoke.

The outlet 84 is defined by a ridged connector nipple 86. As can be best seen in FIG. 4, a length of flexible tubing 90 is removably connected to the ridged connector nipple 86. The outlet 84 is thereby connected in fluid communication via the flexible tubing 90 to a source of low air pressure 92, to thereby permit evacuation of surgical smoke into the inlet 82 of the airflow vent 80, as indicated by arrow "B", through the airflow vent 80, as indicated by arrow "C", and out the outlet 84 of the airflow vent 80, as indicated by arrow "B".

Figure 4:
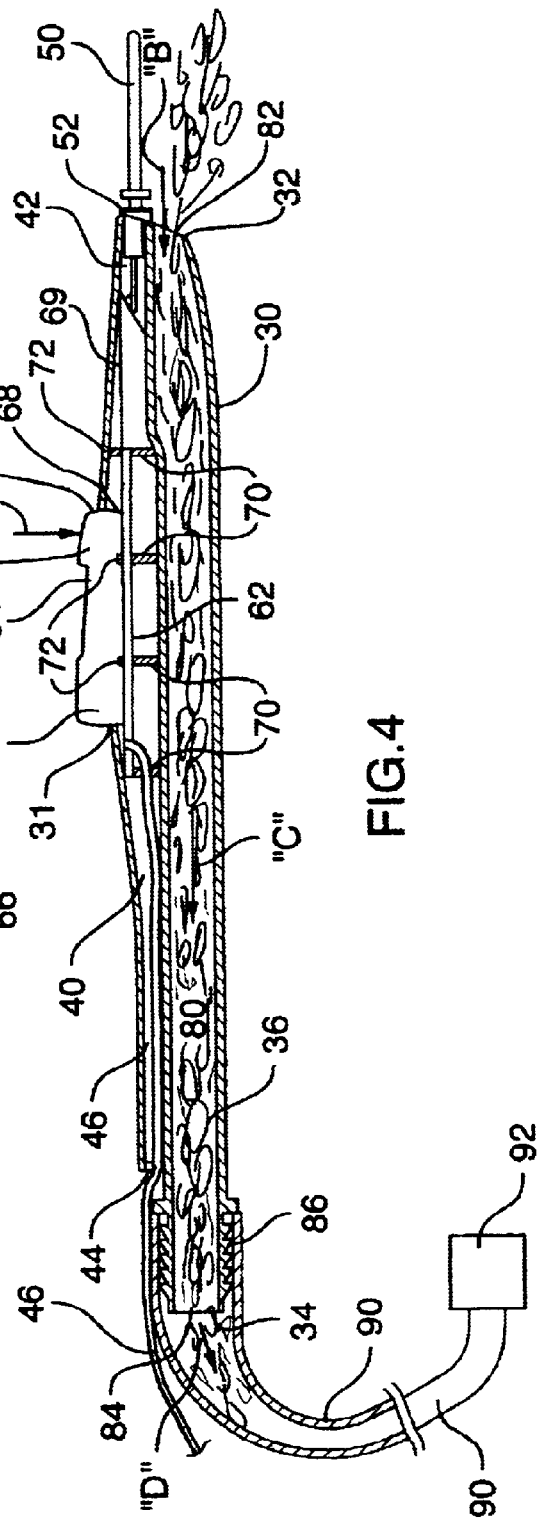
FIG. 4 is a cross-sectional side elevational view similar to FIG. 3, but with a length of flexible tubing connected to the electrosurgical pencil and with the electrosurgical pencil in a smoke evacuating mode.

As can be best seen in FIGS. 3 and 4, the wire-retaining passage 40 and substantially unobstructed airflow vent 80 are substantially parallel one to the other, with the wire-retaining passage 40 being disposed between the rocker type electrical switch 60 and the substantially unobstructed airflow vent 80. Preferably, the cross-sectional area of the substantially unobstructed airflow vent 80 is greater than the cross-sectional area of the wire-retaining passage 40.

In the preferred embodiment, as illustrated in FIGS. 1 through 6, the electrode end 32 of the main body portion 30 is sloped such that the wire-retaining passage 40 extends past the inlet 82 of the substantially unobstructed airflow vent 80.

In an alternative embodiment, as illustrated in FIG. 7, the electrosurgical pencil 120 is similar to the preferred embodiment electrosurgical pencil 20, except that the electrode end 132 of the main body portion 130 is shaped so as to be more transverse to the length of the main body portion 130.

As can be understood from the above description and from the accompanying drawings, the electrosurgical pencil according to the present invention provides a smoke evacuation structure that is integrally formed within the electrosurgical pencil, and that provides maximized air flow, and wherein the air flow path for evacuation of surgical smoke is defined by the main body only, all of which features are unknown in the prior art.

Other variations of the above principles will be apparent to those who are knowledgeable in the field of the invention, and such variations are considered to be within the scope of the present invention. Further, other modifications and alterations may be used in the design and manufacture of the electrosurgical pencil of the present invention without departing from the spirit and scope of the accompanying claims.

I claim:

1. An electrosurgical pencil for use in performing surgery on a surgical site, said electrosurgical pencil comprising:
   a main body portion forming a handle grippable by a user, and having an electrode end and an exhaust end;
   a wire retaining passage disposed within said main body portion and having an electrode-receiving opening and a wire-receiving opening;
   a metal electrode tip mounted on main body portion at said electrode-receiving opening for engaging tissue in a surgical site to thereby cut or coagulate said tissue;
   an electrical switch means mounted on said main body portion so as to be operable externally to said main body portion;
   a wire entering said wire retaining passage through said wire-receiving opening and being selectively connectable in electrically conductive relation through said electrical switch means to said metal electrode tip; and,
   a substantially unobstructed airflow vent disposed within said main body portion and having an inlet disposed adjacent said electrode end of said main body portion and connected in air flow communication via said airflow vent to an outlet disposed adjacent said exhaust end of said main body portion, said substantially unobstructed airflow vent permitting maximized air flow for the removal of surgical smoke;
   wherein said outlet is connectable in fluid communication via flexible tubing to a source of low air pressure, to thereby permit evacuation of surgical smoke into said inlet of said airflow vent, through said airflow vent, and out said outlet of said airflow vent.

2. The electrosurgical pencil of claim 1, wherein said wire retaining passage and said substantially unobstructed airflow vent are each defined by said main body portion.

3. The electrosurgical pencil of claim 1, wherein said wire retaining passage and substantially unobstructed airflow vent are each elongate.

4. The electrosurgical pencil of claim 3, wherein said wire retaining passage and substantially unobstructed airflow vent are substantially parallel one to the other.

5. The electrosurgical pencil of claim 4, wherein said substantially unobstructed airflow vent extends from said electrode end to exhaust end of said main body portion.

6. The electrosurgical pencil of claim 1, wherein said wire retaining passage is disposed between said electrical switch means and said substantially unobstructed airflow vent.

7. The electrosurgical pencil of claim 1, wherein said electrode receiving opening is disposed at said electrode end of said main body portion.

8. The electrosurgical pencil of claim 1, wherein said metal electrode tip is removably mounted on said main body portion.

9. The electrosurgical pencil of claim 1, wherein the cross-sectional area of said substantially unobstructed airflow vent is greater than the cross-sectional area of said wire retaining passage.

10. The electrosurgical pencil of claim 1, wherein said electrode end of said main body portion is sloped such that said wire retaining passage extends past said inlet of said substantially unobstructed airflow vent.

11. An electrosurgical pencil for use in performing surgery on a surgical site, said electrosurgical pencil comprising:
    a main body portion forming a handle grippable by a user, and having an electrode end, and an exhaust end;
    a wire retaining passage defined by said main body portion and having a wire-receiving opening and an electrode-receiving opening;
    a metal electrode tip mounted on main body portion at said electrode-receiving opening for engaging tissue in a surgical site to thereby cut or coagulate said tissue;
    an electrical switch means mounted on said main body portion so as to be operable externally to said main body portion;
    a wire entering said wire retaining passage through said wire-receiving opening and being selectively connectable in electrically conductive relation through said electrical switch means to said metal electrode tip; and,
    an airflow vent defined by said main body portion so as to extend from said electrode end to said exhaust end of said main body portion, and having an inlet disposed adjacent said electrode end of said main body portion and connected in airflow communication via said airflow vent to an outlet disposed adjacent said exhaust end of said main body portion, said substantially unobstructed airflow vent permitting maximized air flow for the removal of surgical smoke;
    wherein said outlet is connectable in fluid communication via flexible tubing to a source of low air pressure, to thereby permit evacuation of smoke into said inlet of said airflow vent, through said airflow vent, and out said outlet of said airflow vent.

12. The electrosurgical pencil of claim 11, wherein said airflow vent is substantially unobstructed.

13. The electrosurgical pencil of claim 11, wherein said wire retaining passage and airflow vent are each elongate.

14. The electrosurgical pencil of claim 13, wherein said wire retaining passage and airflow vent are substantially parallel one to the other.

15. The electrosurgical pencil of claim 11, wherein said wire retaining passage is disposed between said electrical switch means and said airflow vent.

16. The electrosurgical pencil of claim 11, wherein said electrode receiving opening is disposed at said electrode end of main body portion.

17. The electrosurgical pencil of claim 11, wherein said metal electrode tip is removably mounted on main body portion.

18. The electrosurgical pencil of claim 11, wherein the cross-sectional area of said airflow vent is greater than the cross-sectional area of said wire retaining passage.

19. The electrosurgical pencil of claim 11, wherein said electrode end of said main body portion is sloped such that said wire retaining passage extends past said inlet of said airflow vent.

20. An electrosurgical pencil for use in performing surgery on a surgical site, said electrosurgical pencil comprising:
   a main body portion forming a handle grippable by a user, and having an electrode end and an exhaust end;
   a wire retaining passage disposed within said main body portion and having an electrode-receiving opening and a wire-receiving opening;
   a metal electrode tip mounted on main body portion at said electrode-receiving opening for engaging tissue in a surgical site to thereby cut or coagulate said tissue;
   an electrical switch means mounted on said main body portion so as to be operable externally to said main body portion;
   a wire entering said wire retaining passage through said wire-receiving opening and being selectively connectable in electrically conductive relation through said electrical switch means to said metal electrode tip; and,
   an airflow vent substantially solely defined by said main body portion, said airflow vent having an inlet disposed adjacent said electrode end of said main body portion and connected in air flow communication via said airflow vent to an outlet disposed adjacent said exhaust end of said main body portion, said substantially unobstructed airflow vent permitting maximized air flow for the removal of surgical smoke;
   wherein said outlet is connectable in fluid communication via flexible tubing to a source of low air pressure, to thereby permit evacuation of surgical smoke into said inlet of said airflow vent, through said airflow vent, and out said outlet of said airflow vent.

21. The electrosurgical pencil of claim 20, wherein said main body portion comprises two components.

22. The electrosurgical pencil of claim 11, wherein said airflow vent is substantially unobstructed.

23. The electrosurgical pencil of claim 20, wherein said wire retaining passage and substantially unobstructed airflow vent are each elongate.

24. The electrosurgical pencil of claim 23, wherein said wire retaining passage and substantially unobstructed airflow vent are substantially parallel one to the other.

25. The electrosurgical pencil of claim 24, wherein said substantially unobstructed airflow vent extends from said electrode end to said exhaust end of said main body portion.

26. The electrosurgical pencil of claim 20, wherein said wire retaining passage is disposed between said electrical switch means and said substantially unobstructed airflow vent.

27. The electrosurgical pencil of claim 20, wherein said electrode receiving opening is disposed at said electrode end of main body portion.

28. The electrosurgical pencil of claim 20, wherein said metal electrode tip removably mounted on main body portion.

29. The electrosurgical pencil of claim 20, wherein the cross-sectional area of said substantially unobstructed airflow vent is greater than the cross-sectional area of said wire retaining passage.

30. The electrosurgical pencil of claim 20, wherein said electrode end of said main body portion is sloped such that said wire retaining passage extends past said inlet of said substantially unobstructed airflow vent.

* * * * *